United States Patent [19]

Viers

[11] Patent Number: 4,705,504
[45] Date of Patent: Nov. 10, 1987

[54] BREAST PUMP

[76] Inventor: Karen A. Viers, 31133 Windsor, Westland, Mich. 48185

[21] Appl. No.: 945,688

[22] Filed: Dec. 23, 1986

[51] Int. Cl.$^4$ .............................................. A61M 1/06
[52] U.S. Cl. ....................................... 604/75; 604/346
[58] Field of Search ..................................... 604/74–76, 604/185, 315–316, 346

[56] References Cited

U.S. PATENT DOCUMENTS

| 85,318 | 12/1868 | Mattson | 604/75 |
| 316,584 | 4/1885 | Turner | 604/75 |
| 949,258 | 2/1910 | Brumley | 604/75 |
| 3,911,920 | 10/1975 | Susinn | 604/75 |
| 4,501,585 | 2/1985 | Friedman | 604/346 |

Primary Examiner—Dalton L. Truluck
Attorney, Agent, or Firm—Charles W. Chandler

[57] ABSTRACT

A breast pump having a hollow, squeezable, resilient suction member with an inlet opening for accommodating a nipple and receiving a liquid into the suction member as it is being inflated, and a discharge opening for discharging liquid into a disposable bag as the suction member is being squeezed. The pump is relatively small to fit into a lady's purse when not in use.

3 Claims, 3 Drawing Figures

BREAST PUMP

BACKGROUND OF THE INVENTION

This invention is related to breast pumps and more particularly to a breast pump in which the liquid is passed through the suction member and then discharged into a disposable bag.

Breast pumps have been used for a long period of time, see for example: U.S. Pat. No. 11,623 which issued to E. Waters on Aug. 29, 1854; U.S. Pat. No. 603,564 which issued to J. H. Hoover on May 3, 1898; and U.S. Pat. No. 69,570 which issued to M. Mattson on Oct. 8, 1967. A relatively modern-day breast pump is illustrated in U.S. Pat. No. 4,323,067 which issued to Frank H. Adams on Apr. 6, 1982.

A common problem with many breast pumps is that they cannot be conveniently carried by the user in her purse because of their size. One reason is that they are usually formed with a suction member and a reservoir for receiving the liquid. Usually the reservoir is a relatively rigid member requiring a considerable amount of space.

SUMMARY OF THE INVENTION

The broad purpose of the present invention is to provide a compact breast pump in which the suction member comprises a squeezable, resilient hollow member having an inlet opening to receive a liquid into a temporary position within the suction member as it is being inflated, and a discharge opening for discharging the liquid as the suction member is being squeezed. A disposable plastic bag is mounted on the suction member about the discharge opening to provide means for disposing of the liquid. One of the advantages of the invention is that the disposable bag requires relatively little storage space because it can be rolled up or folded until it is used. In addition, it is not a permanent part of the suction member. The suction member requires a relatively small amount of storage space, can be easily cleaned, easily stored and inexpensively manufactured.

Still further objects and advantages of the invention will become readily apparent to those skilled in the art to which the invention pertains upon reference to the following detailed description.

DESCRIPTION OF THE DRAWING

The description refers to the accompanying drawing in which like reference characters refer to like parts throughout the several views and, in which.

DESCRIPTION OF THE PREFERRED EMBODIMENT

Figure 1:
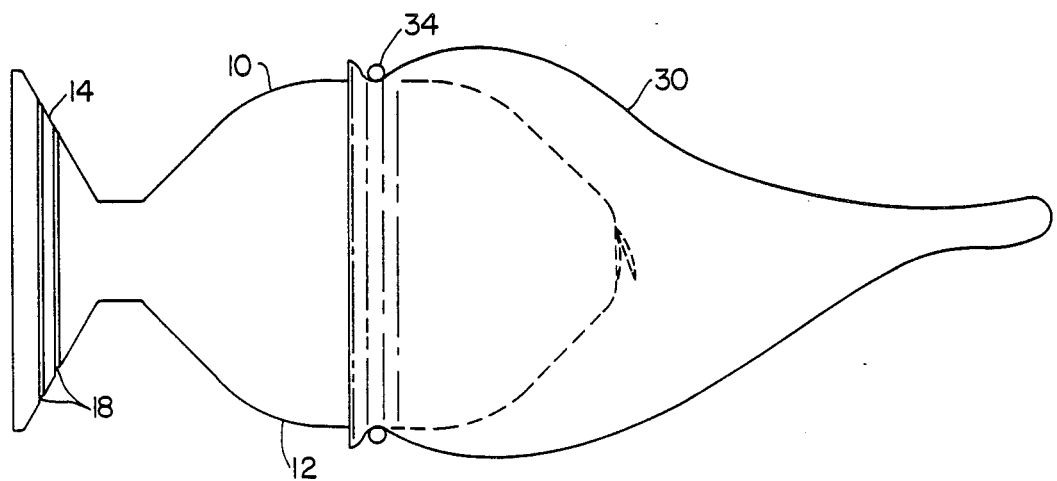
FIG. 1 is a view of a breast pump illustrating the preferred embodiment of the invention.

Referring to the drawing, a preferred breast pump 10 comprises a resilient, squeezable, hollow, suction member 12 having a frusto-conical end 14 defining an inlet opening 16. End 14 has a plurality of annular score lines 18 so that the user can trim the open end to a diameter accommodating the size of the user's nipple and to provide a sealing connection between the breast pump and the user. Suction member 12 may be formed of a blow molded plastic such as polyethylene, an elastomer or a polyolefin.

Suction member 12 has an internal reservoir 20 for a liquid being received through opening 16. The opposite, discharge end of the suction member has a discharge opening 22 for discharging the liquid from the reservoir. A flap or valve 24 is mounted over the discharge opening and attached to the suction member so that the valve is moveable from the closed position illustrated at "A" to an open position illustrated at "B" to pass the liquid from the reservoir. The discharge end of the suction member has a somewhat tapered or conical configuration to aid the liquid in flowing toward the discharge opening so that it does not become trapped in the reservoir. The shape also makes the suction member easier to clean.

Figure 3:
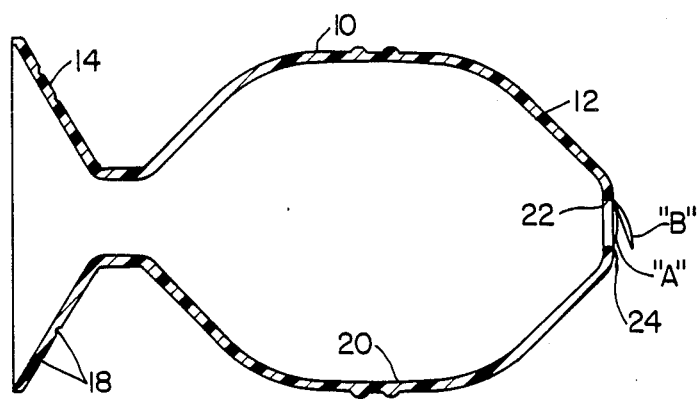
FIG. 3 is a longitudinal sectional view through the suction member.

Suction member 12 is squeezable so that when the user squeezes it to reduce its volume with the inlet opening blocked by the nipple, valve 24 opens to discharge the liquid. When the squeezing motion is removed, valve 24 then closes to provide a negative pressure in the reservoir as the suction member expands toward its normal, unsqueezed condition, illustrated in FIG. 3 to draw in the milk.

Figure 2:
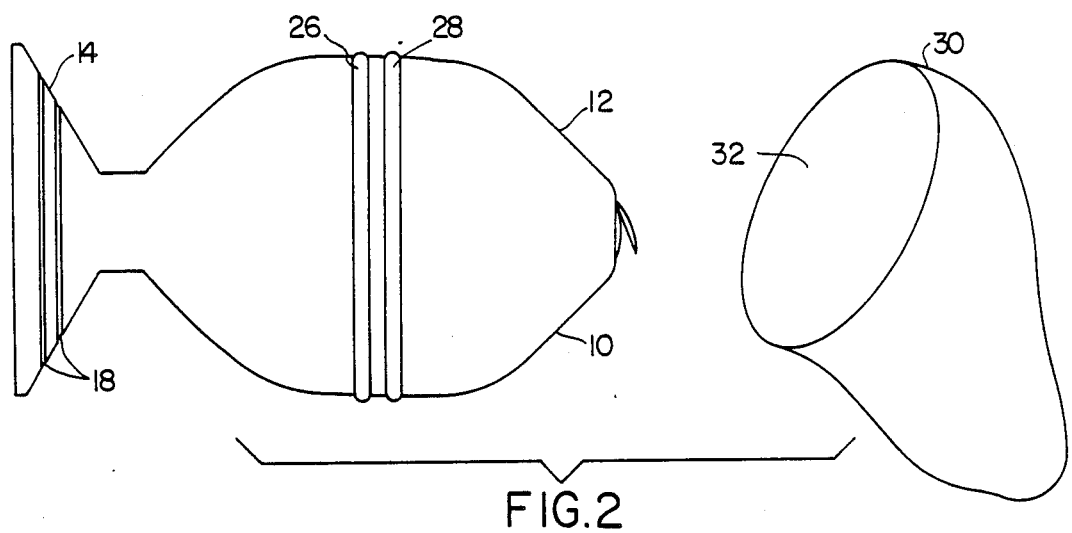
FIG. 2 is a view showing the breast pump separated from the disposable bag.

Referring to FIG. 2, the midsection of the suction member 12 has a pair of closely spaced annular ridges 26 and 28. The ridges function to strengthen the midsection of the suction member.

A flexible, disposable, plastic bag 30 is employed with the suction member. Bag 30 has an open end 32 mounted over ridges 26 and 28, and rubber band 34 is mounted around the bag edge to connect the bag to the suction member as it is being used. Bag 30, is preferably a commercially-available baby bottle plastic bag.

The breast pump may be carried in the user's purse or in other suitable storage locations. In order to use it, the user employs rubber band 34 to mount the bag on the suction member. After mounting the suction member on her breast, the user squeezes the suction member in the conventional manner, discharging the contents of the reservoir, which functions as a temporary storage location for the liquid, into the disposable bag. When she releases the suction member, it assists in drawing in milk through the inlet opening as the suction member expands. She can then dispose of the bag 30, clean the suction member, if necessary, and return it to her purse.

Having described my invention, I claim:

1. A breast pump, comprising:

a resilient, squeezable, hollow, suction member, having an inlet opening, a discharge opening, and reservoir means between the inlet opening and the discharge opening, the suction member being inflatable after being squeezed, so as to apply a negative pressure on the inlet opening;

means mounted on the suction member adjacent the inlet opening for receiving a nipple in a sealing relationship;

valve means mounted in the discharge opening for removal of a liquid from the reservoir means as the suction member is being deflated by a squeezing motion, and for receiving a liquid through the inlet opening as the suction member is being inflated;

a disposable, removable bag having an opening suited for receiving a portion of the suction member about the discharge opening; and means on the suction member for retaining the opening of the removable bag around the portion of the suction member such that liquid from the reservoir means is discharged to the removable bag as the suction member is being deflated.

2. A breast pump as defined in Claim 1, in which the valve means includes a valve member that is movable to an open position to permit a liquid to flow through the discharge opening, and to a closed position to create a negative pressure in the suction member.

3. A breast plump, comprising:

a hollow, squeezable, suction member having a frusto-conical inlet opening adapted to receive a nipple, and adapted to be cut to accommodate the dimensions of the nipple and to form a sealing relationship therewith;

annular structure about said suction member between the inlet opening and the discharge opening;

reservoir means in the suction member between the inlet opening and the discharge opening;

valve means mounted on the suction member so as to permit a liquid in the reservoir means to discharge through the discharge opening at such times as the suction member is being squeezed; and a disposable bag mounted about the discharge opening for receiving a liquid being discharged through the discharge opening.

\* \* \* \* \*